(12) United States Patent
Rüdenauer et al.

(10) Patent No.: US 9,340,754 B2
(45) Date of Patent: May 17, 2016

(54) PROCESS FOR THE PREPARATION OF CYCLOHEXYL-SUBSTITUTED TERTIARY ALKANOLS

(71) Applicant: BASF SE, Ludwigshafen (DE)

(72) Inventors: Stefan Rüdenauer, Worms (DE); Ralf Pelzer, Ludwigshafen (DE); Klaus Ebel, Heddesheim (DE); Martin Bock, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/090,626

(22) Filed: Nov. 26, 2013

(65) Prior Publication Data

US 2014/0163117 A1  Jun. 12, 2014

Related U.S. Application Data

(60) Provisional application No. 61/730,104, filed on Nov. 27, 2012.

(51) Int. Cl.
| | |
|---|---|
| C11D 3/50 | (2006.01) |
| A61K 8/34 | (2006.01) |
| C07C 29/19 | (2006.01) |
| C07C 29/44 | (2006.01) |
| C07C 33/20 | (2006.01) |
| C11D 3/20 | (2006.01) |
| A61Q 19/00 | (2006.01) |

(52) U.S. Cl.
CPC ............. C11D 3/2065 (2013.01); A61K 8/34 (2013.01); A61Q 19/00 (2013.01); C07C 29/19 (2013.01); C07C 29/44 (2013.01); C11D 3/2024 (2013.01); C11D 3/50 (2013.01); C07C 2101/14 (2013.01)

(58) Field of Classification Search
CPC ...... C11D 3/2024; C11D 3/50; C11D 3/2065; C11D 3/20; A61K 8/34; C07D 31/135; C07C 31/1355; C07C 29/36; C07C 29/19; C07C 29/44; C07C 33/20
USPC ........ 514/772; 510/276, 505; 512/1; 568/829
See application file for complete search history.

(56) References Cited

U.S. PATENT DOCUMENTS

| | | | |
|---|---|---|---|
| 3,027,398 A | 3/1962 | Foohey | |
| 4,701,278 A | 10/1987 | Fehr | |
| 4,847,394 A | 7/1989 | Schuster | |
| 5,936,126 A | 8/1999 | Ruhl et al. | |
| 7,208,545 B1 | 4/2007 | Brunner et al. | |
| 8,450,534 B2 * | 5/2013 | Ebel et al. | 568/822 |
| 9,056,812 B2 * | 6/2015 | Schuch et al. | |
| 2002/0019559 A1 | 2/2002 | Brunner et al. | |
| 2004/0097752 A1 | 5/2004 | Lettmann et al. | |
| 2004/0199033 A1 | 10/2004 | Bottcher et al. | |
| 2006/0183936 A1 | 8/2006 | Grass et al. | |
| 2007/0112210 A1 | 5/2007 | Arndt et al. | |
| 2007/0149793 A1 | 6/2007 | Arndt et al. | |
| 2010/0152436 A1 | 6/2010 | Laar et al. | |
| 2012/0296111 A1 | 11/2012 | Konigsmann et al. | |

FOREIGN PATENT DOCUMENTS

| | | |
|---|---|---|
| DE | 4407091 C1 | 8/1995 |
| EP | 258789 A2 | 3/1988 |
| EP | 0813906 A2 | 12/1997 |
| EP | 1420012 A1 | 5/2004 |
| EP | 2512658 A2 | 10/2012 |
| EP | 09179201.0 | 10/2012 |
| WO | WO-99/32427 A1 | 7/1999 |
| WO | WO-00/78704 A1 | 12/2000 |
| WO | WO-02/100536 A1 | 12/2002 |
| WO | WO-03/103830 A1 | 12/2003 |
| WO | WO-2005/061105 A1 | 7/2005 |
| WO | WO-2005/061106 A1 | 7/2005 |
| WO | WO-2006/136541 A2 | 12/2006 |
| WO | WO-2011082991 A2 | 7/2011 |
| WO | WO-2011117360 A2 | 9/2011 |

OTHER PUBLICATIONS

Sobotka et al., caplus an 1949:6343.*
Dazlauskas, caplus an 1968:418654.*
Ruan et al., caplus an 2010:357097 (2010).*
Denutte et al., caplus an 2010:1436121 (2010).*
Dazlauskas, (1968), caplus an 1968:418654.*

* cited by examiner

Primary Examiner — Sun Jae Yoo
(74) Attorney, Agent, or Firm — Drinker Biddle & Reath LLP

(57) ABSTRACT

The present invention relates to processes for the preparation of compounds of the formula (Ia)

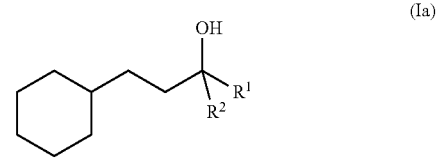

(Ia)

by reacting styrene with a secondary alkanol and the hydrogenation of the resulting phenyl-substituted tertiary alkanol. In addition, the invention relates to compounds of the formula (Ia) and to the use of such compounds as fragrances, and also to compositions which comprise compounds of the formulae (Ia) and (Ib).

15 Claims, No Drawings

PROCESS FOR THE PREPARATION OF CYCLOHEXYL-SUBSTITUTED TERTIARY ALKANOLS

CROSS-REFERENCE TO RELATED APPLICATIONS

This application claims benefit (under 35 USC 119(e)) of U.S. Provisional Application 61/730,104, filed Nov. 27, 2012, which is incorporated by reference.

The present invention relates to a process for the preparation of cyclohexyl-substituted tertiary alkanols, and to the use of such compounds as fragrance.

Fragrances are used in a large number of technical products and household products for concealing undesired intrinsic odors or for olfactory improvement. Floral notes are of great interest here, especially for use in detergents and cleaners. It is important for uses of this type that the fragrances not only have a pleasant odor but also remain chemically stable even over a prolonged period and can be incorporated in a technically easy manner into the corresponding product. The availability of as cost-effective as possible a production process for the fragrances is also desirable.

4-Cyclohexyl-2-methyl-2-butanol, which is also referred to as coranol, is a fragrance with a lily of the valley scent, the use of which as a constituent of scent compositions was described for the first time in U.S. Pat. No. 4,701,278. Preparation processes for 4-cyclohexyl-2-methyl-2-butanol have been described by Okazawa et al. (Can. J. Chem. 60 (1982), 2180-93) and Ebel et al. (WO 2011/117360).

In principle, there is a continuing need for new fragrances to supplement the existing pallet of fragrances. In searching for new fragrances which meet the aforementioned requirements, it has now surprisingly been found that cyclohexyl-substituted tertiary alkanols such as 1-cyclohexyl-3-methyl-3-pentanol and its relatively long-chain analogs have interesting olfactory properties. As well as a pleasant lavender note (similar to coranol, tetrahydrolinalool), 1-cyclohexyl-3-methyl-3-pentanol, for example, additionally has fruity aspects.

Furthermore, a new process for the preparation of such compounds has been found. Synthesis routes for obtaining 1-cyclohexyl-3-methyl-3-pentanol are described by Dazlauskas (Chemiya, Technika, Fizine Geografiya (4): 35-42, 1967) and also Nazarov and Nagibina (Izvestiya Akademii Nauk SSSR, Seriya Khimicheskaya: 83-89, 1946). However, these production pathways involve many stages and would consequently be associated with high costs in the event of practical conversion to an industrial scale.

The present invention provides a process for the preparation of a compound of the formula (Ia)

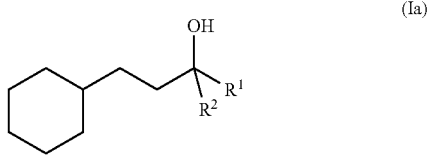
(Ia)

comprising:
a) the reaction of styrene with a compound of the formula (II)

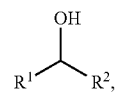
(II)

giving a compound of the formula (IIIa)

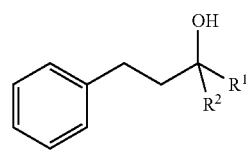
(IIIa)

and
b) the heterogeneous-catalytic hydrogenation of the compound of the formula (IIIa) to give the compound of the formula (Ia).

Unless stated otherwise, in the compounds of the formulae (Ia), (Ib), (II), (IIIa), (IIIb), (IV) and (V) described here and below, $R^1$ and $R^2$, independently of one another, are selected from groups of the formula $(C_{3-7}\text{-cycloalkyl})_x\text{-}(C_{1-7}\text{-alkyl})_y$, wherein either each of x and y is 1, or one of the variables x and y is 1 and the other is 0. Preferably, $R^1$ and $R^2$, independently of one another, are selected from $C_{1-7}$-alkyl, $C_{3-7}$-cycloalkyl and $C_{4-7}$-cycloalkylalkyl. Here, $R^1$ and $R^2$ together comprise in total 3 to 11 carbon atoms, in particular 3 to 8 carbon atoms, preferably 3 to 5 carbon atoms and particularly preferably 3 carbon atoms.

As used here, $C_{1-7}$-alkyl is a linear or branched alkyl radical having 1 to 7 carbon atoms. Examples of linear $C_{1-7}$-alkyl are methyl, ethyl, n-propyl, n-butyl, n-pentyl and n-hexyl. Examples of branched $C_{1-7}$-alkyl are isopropyl, sec-butyl, tert-butyl, isohexyl, 1-methylpentyl, 2-methylpentyl, 3-methylpentyl, 1,1-dimethylbutyl, 2,2-dimethylbutyl, 3,3-dimethylbutyl and 2-ethylbutyl.

As used here, $C_{3-7}$-cycloalkyl is a cycloalkyl radical having in total 3 to 7 carbon atoms which is bonded via one of the carbon ring atoms. This cycloalkyl radical is not substituted or is substituted with 1, 2 or 3 $C_{1-7}$-alkyl radicals, as defined above, with the proviso that the cycloalkyl radical comprises in total (i.e. including any alkyl substituents) not more than 7 carbon atoms. Examples of an unsubstituted $C_{3-7}$cycloalkyl are cyclopropyl, cyclobutyl, cyclopentyl and cyclohexyl.

As used here, $C_{4-7}$-cycloalkylalkyl is a cycloalkyl group-substituted linear or branched alkyl radical which comprises in total (i.e. including the cycloalkyl substituent) 4 to 7 carbon atoms. Examples of $C_{4-7}$-cycloalkylalkyl are cyclohexylmethyl, cyclopentylmethyl and 1-cyclopentylethyl.

According to one preferred aspect of the invention, $R^1$ and $R^2$, independently of one another, are selected from $C_{1-7}$-alkyl and $C_{3-7}$-cycloalkyl. The respective compounds within one specific reaction route of the described reaction routes (also referred to below as "corresponding compounds") carry the same $R^1$ and $R^2$.

A preferred embodiment of the invention relates to a process for the preparation of 1-cyclohexyl-3-methyl-3-pentanol, comprising:
a) the reaction of styrene with 2-butanol, giving 3-methyl-1-phenyl-3-pentanol, and
b) the heterogeneous-catalytic hydrogenation of 3-methyl-1-phenyl-3-pentanol to give 1-cyclohexyl-3-methyl-3-pentanol.

In further embodiments of the process according to the invention, the compound of the formula (Ia) is selected from 1-cyclohexyl-3-methyl-3-hexanol, 1-cyclohexyl-3-methyl-3-heptanol, 1-cyclohexyl-3-methyl-3-octanol, 1-cyclohexyl-3-methyl-3-nonanol, 1-cyclohexyl-3,4-dimethyl-3-octanol, 1-cyclohexyl-3,5-dimethyl-3-octanol, 1-cyclohexyl-3,6-dimethyl-3-octanol, 1-cyclohexyl-3,7-dimethyl-3-octanol, 1-cyclohexyl-3,4,4-trimethyl-3-heptanol, 1-cyclohexyl-3,5,5-trimethyl-3-heptanol, 1-cyclohexyl-3,6,6-trimethyl-3-heptanol, 1-cyclohexyl-5-ethyl-3-methyl-3-heptanol, 1-cyclohexyl-3,5-dimethyl-3-heptanol, 2,4-dicyclohexyl-2-methyl-2-butanol, 1-cyclohexyl-4-cyclopentyl-3-methyl-3-pentanol, 1-cyclohexyl-3-ethyl-3-hexanol, 1-cyclohexyl-3-ethyl-3-heptanol, 1-cyclohexyl-3-ethyl-3-octanol and 1-cyclohexyl-3-ethyl-3-nonanol.

The process for the preparation of the compound of the formula (Ia) can be depicted by the following reaction scheme:

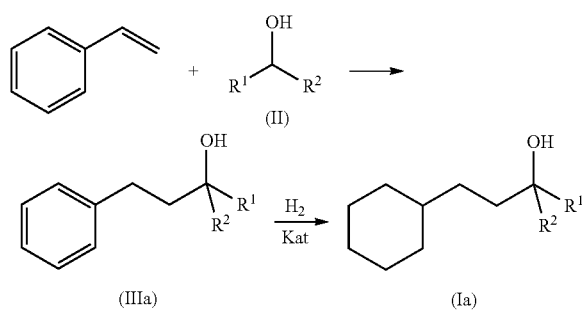

The invention thus relates to a process for the preparation of a compound of the formula (Ia) with the steps described here and below and also in the claims.

The process is associated with a number of advantages. It permits an extremely high atom-economic preparation of a compound of the formula (Ia) from very inexpensive basic chemicals, manages without complex work-up steps and is consequently comparatively cost-effective. The use of expensive and hazardous reagents such as methyllithium is not required.

Both step a) and step b) can be carried out without problems on an industrial scale and produce the respective products with high selectivity and good yields. In step a) of the process according to the invention, a secondary alkanol of the formula (II) is reacted with styrene. Here, in the sense of a hydroxyalkylation, a corresponding phenyl-substituted tertiary alkanol of the formula (IIIa) is formed, and also, as by-products, inter alia toluene and ethylbenzene, although these can be separated off from the target product for example by distillation.

Furthermore, in step a), besides the compound of the formula (IIIa), the corresponding (i.e. identical $R^1$, $R^2$) methyl-substituted alkanol of the formula (IIIb)

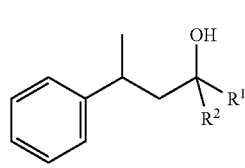

can be formed, from which, as a result of heterogeneous-catalytic hydrogenation, the compound of the formula (Ib)

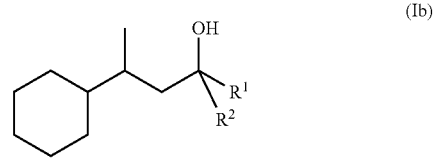

arises.

The methyl-substituted alkanol of the formula (IIIb) arises presumably as a result of the reaction of the compound of the formula (II) with α-methylstyrene, which can be formed in a radical reaction according to the following scheme from styrene and ethylbenzene:

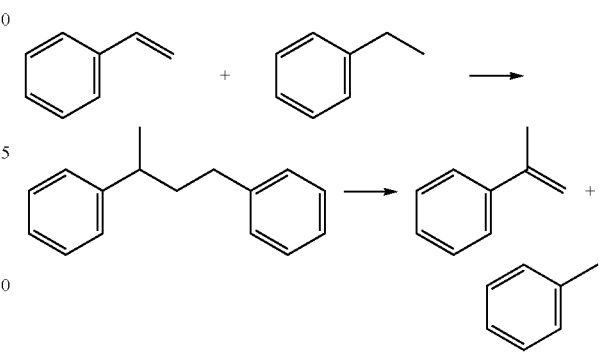

With regard to the selectivity of the reaction, it has proven to be advantageous if the reaction in step a) is carried out under supercritical conditions. These are understood as meaning reaction conditions under which at least one of the components of the reaction mixture, preferably the compound of the formula (II), is present in the supercritical state. Accordingly, according to a preferred embodiment of the process according to the invention, the reaction in step a) takes place under conditions under which the compound of the formula (II) is present in the supercritical state. In the case of 2-butanol, for example, the critical temperature $T_c$ is 263° C. and the critical pressure $P_c$ is 4.2 MPa. Supercritical conditions can be adjusted by the person skilled in the art by varying the pressure and temperature.

The temperature required for an adequate rate of the reaction of styrene with a compound of the formula (II) is generally at least $(T_c+15)°$ C., often at least $(T_c+65)°$ C. and in particular at least $(T_c+85)°$ C., where $T_c$ is the critical temperature of the compound of the formula (II) used. To achieve an adequate selectivity of the reaction, it has proven to be advantageous if the temperature during the reaction in step a) does not exceed a value of $(T_c+265)°$ C., in particular $(T_c+165)°$ C. The reaction in step a) preferably takes place at increased pressure, which is generally in the range from 5 to 50 MPa, often in the range from 10 to 30 MPa and in particular in the range from 15 to 25 MPa. Preferably, the reaction takes place under the intrinsic pressure of the reaction mixture prevailing at the desired reaction temperature.

The reaction time naturally depends on the selected conditions and the desired conversion and is usually in the range from 30 s to 4 h, in particular in the range from 3 min to 3 h and specifically in the range from 5 min to 2.5 h. In one embodiment of the invention, the reaction time is in the range from 0.5 to 4 h, in particular in the range from 1 to 3 h and specifically in the range from 1.5 to 2.5 h. As a rule, the reaction is carried out until the reactant used in deficit, which is preferably styrene, has been reacted to at least 80%, in particular to at least 90%.

It has proven to be particularly advantageous to carry out the reaction in step a) at elevated temperatures, i.e. above $(T_c+65)°$ C., in particular above $(T_c+85)°$ C., preferably in the range $(T_c+115)°$ C. and $(T_c+165)°$ C. This allows short reaction times which are usually in the range from 30 s to 30 min, in particular in the range from 3 min to 20 min and specifically in the range from 5 min to 15 min. In this way, good selectivities as regards the target product can also be achieved for a high conversion of styrene.

With regard to the selectivity of the reaction, it has proven to be advantageous if the reaction in step a) is carried out in the extensive or complete absence of catalysts, such as, for example, radical starters, acids or transition metal compounds. Extensive absence means that the concentration of any catalysts is less than 1 g/kg (<1000 ppm), in particular less than 0.1 g/kg (<100 ppm), based on the total weight of the reaction mixture.

The reaction of styrene with a compound of the formula (II) in step a) can be carried out without dilution or in a diluent that is suitable, i.e. inert under reaction conditions. Suitable inert diluents are aprotic organic solvents which have no ethylenically unsaturated double bond, such as, for example, aliphatic and alicyclic ethers having preferably 4, 5 or 6 carbon atoms, e.g. diethyl ether, 1,2-dimethoxyethane, bis(2-methoxyethyl) ether, 2-methyltetrahydrofuran and in particular tetrahydrofuran; aliphatic and cycloaliphatic saturated hydrocarbons having preferably 5 to 8 carbon atoms, e.g. pentane, hexane, heptane or octane; alkyl esters of aliphatic carboxylic acids having preferably 4 to 8 carbon atoms and mixtures of the aforementioned solvents. Preferably, the reaction in step a) takes place without dilution, i.e. essentially no feed materials different from styrene and the compound of the formula (II), such as, for example, inert solvents, are used for the reaction. Essentially here means that styrene and the compound of the formula (II) constitute at least 95% by weight, in particular at least 99% by weight, based on the total amount of the components used in step a). In addition, the reactants used for the reaction, i.e. styrene and the compound of the formula (II), may comprise, as a result of manufacture, small amounts of impurities such as water, ethylbenzene, toluene and the like, the contaminants generally constituting less than 5% by weight, in particular less than 1% by weight, based on the total amount of the reactants. In particular, the water content of the reactants used in step a) is not more than 1% by weight, based on the total amount of the reactants.

As regards the selectivity of the reaction, it has proven to be advantageous if, in the reaction according to step a), a compound of the formula (II) is used in large excess, based on styrene, and/or it is ensured that, in the reaction zone in which styrene and the compound of the formula (II) are brought into contact with one another under reaction conditions, there is a high excess of the compound of the formula (II), based on the styrene located in the reaction zone. As a rule, in step a), styrene and the compound of the formula (II) are reacted in a molar ratio of styrene to compound of the formula (II) of at most 1:5, preferably at most 1:10, in particular at most 1:30, particularly preferably at most 1:40 and specifically at most 1:50. With regard to an efficient reaction procedure, it is advantageous if, in step a), styrene and compound of the formula (II) are used in a molar ratio in the range from 1:5 to 1:200, preferably in the range from 1:10 to 1:200, in particular in the range from 1:30 to 1:150 or in the range from 1:30 to 1:130, particularly preferably in the range from 1:40 to 1:100 and specifically in the range from 1:50 to 1:90.

The reaction in step a) can be carried out batchwise (so-called batch mode), i.e. the styrene and the compound of the formula (II) are introduced as initial charge in the desired molar ratio in a suitable reactor and brought to the desired reaction conditions and held under reaction conditions until the desired conversion is attained. The reaction in step a) can also be carried out in the so-called semi-batch mode, i.e. the majority, as a rule at least 80%, in particular at least 90%, of one or both reactants, is added to the reactor under reaction conditions continuously or in portions over an extended period, generally at least 50% of the total reaction time. For example, at least 80%, in particular at least 90%, of the compound of the formula (II) used, optionally together with some of the styrene, can be introduced as initial charge, and at least 80%, in particular at least 90%, of the styrene used can be supplied to the reaction under reaction conditions.

The reaction in step a) can also be carried out continuously, i.e. styrene and compound of the formula (II) are fed continuously into a reaction zone in the desired molar ratio and the reaction mixture is removed continuously from the reaction zone. The rate at which styrene and compound of the formula (II) are supplied to the reaction zone is governed by the desired residence time, which for its part depends in a known manner on the reactor geometry and corresponds to the reaction time stated above.

The reaction in step a) can in principle be carried out in all reactors which are suitable for the selected reaction conditions, preferably in autoclaves, which can have devices for mixing the reactants, or in reaction tubes.

In order to keep the molar ratio of styrene to compound of the formula (II) low during the reaction and at the same time to permit an efficient reaction procedure, it has proven to be advantageous if at least 80%, in particular at least 90%, of the compound of the formula (II) used in step a), optionally together with some of the styrene, is introduced as initial charge, and at least 80%, in particular at least 90%, of the styrene used in step a) is supplied to the reaction in step a) under reaction conditions. The addition of the styrene can take place in portions or preferably continuously. The rate at which styrene is supplied here is preferably selected such that the molar ratio of the still unreacted styrene fed into the reaction zone or the reactor to the compound of the formula (II) located in the reaction zone during the reaction is less than 1:10, in particular not more than 1:40 and specifically not more than 1:50 and is e.g. in the range from 1:10 to 1:2000, preferably in the range from 1:40 to 1:1500 and in particular in the range from 1:50 to 1:1000. In the case of a continuous reaction procedure, styrene and compound of the formula (II) will therefore be supplied to the reactor or the reaction zone in the aforementioned molar ratios. In a specific embodiment of the invention, the rate at which styrene is supplied is preferably selected such that the molar ratio of the styrene fed into the reaction zone or the reactor to the compound of the formula (II) located in the reaction zone is in the range from 1:10 to 1:130, in particular in the range from 1:20 to 1:120, particularly preferably in the range from 1:40 to 1:100 and specifically in the range from 1:50 to 1:90. This is the case in particular also for a continuous reaction procedure for the molar ratios of styrene and compound of the formula (II) supplied to the reactor or the reaction zone.

The reaction mixture obtained in step a) can be worked up in a manner known per se or, optionally after removing the compound of the formula (II), be used directly as such in step b) of the process according to the invention. As a rule, it has proven to be advantageous to work up the reaction mixture produced in step a), for example extractively or distillatively or by a combination of these measures. In one embodiment of the process according to the invention, the reaction mixture produced in step a) is worked up distillatively, in which case the desired compound of the formula (IIIa) or the desired composition consisting essentially of the compound of the formula (IIIa) and the corresponding compound of the formula (IIIb) is separated off as middle fraction from low boilers and high boilers. If an excess of compound of the formula (II) is used in the process, the low boiling fraction, which consists predominantly of compound of the formula (II), can be returned to the process. As a rule, prior to step b), the compound of the formula (II) will be largely removed, such that the fraction of compound of the formula (II) in the starting material used for the hydrogenation in step b) is less than 20% by weight, in particular not more than 10% by weight, based on the total amount of starting material in step b).

Depending on the configuration of the distillation, the essentially pure compound of the formula (IIIa) (purity at least 95% by weight, in particular at least 98% by weight and specifically at least 99% by weight or at least 99.5% by weight) or a composition which consists essentially, i.e. to at least 95% by weight, in particular at least 98% by weight and specifically at least 99% by weight or at least 99.5% by weight, of compound of the formula (IIIa) and corresponding compound of the formula (IIIb), where the molar ratio of the compound of the formula (IIIa) to the corresponding compound of the formula (IIIb) is typically in the range from 50:1 to 1000:1 is/are obtained.

Both the pure compound of the formula (IIIa) and also the composition can be used in the subsequent hydrogenation according to step b). This gives rise to the corresponding pure compound of the formula (Ia) (purity at least 95% by weight, in particular at least 98% by weight and specifically at least 99% by weight or at least 99.5% by weight) or the corresponding composition of compound of the formula (Ia) and compound of the formula (Ib) (purity and weight ratio of the compounds of the formulae (Ia) and (Ib) essentially as defined above for the compounds of the formulae (IIIa) and (IIIb)).

The hydrogenation expediently takes place over a catalyst suitable for the ring hydrogenation of aromatics, which is also referred to below simply as catalyst. Suitable catalysts are in principle all catalysts which are known to be suitable for the ring hydrogenation of aromatics, i.e. catalysts which catalyze the hydrogenation of phenyl groups to cyclohexyl groups. These are usually catalysts which comprise at least one active metal from group VIIIB of the Periodic Tables (CAS version), such as e.g. palladium, platinum, cobalt, nickel, rhodium, iridium, ruthenium, in particular ruthenium, rhodium or nickel, or comprise a mixture of two or more thereof, optionally in combination with one or more further active metals. Preferred further active metals are selected from groups IB or VIIB of the Periodic Tables (CAS version). Among the metals of subgroups IB and/or VIIB that can likewise be used, e.g. copper and/or ruthenium are suitable.

The catalysts can be unsupported catalysts or, preferably, supported catalysts. Suitable support materials are, for example, activated carbon, silicon carbide, silicon dioxide, aluminum oxide, magnesium oxide, titanium dioxide, zirconium dioxide, aluminosilicates and mixtures of these support materials. The amount of active metal is usually 0.05 to 10% by weight, often 0.1 to 7% by weight and in particular 0.1 to 5% by weight, based on the total weight of the supported catalyst, particularly if the active metal is a precious metal such as rhodium, ruthenium, platinum, palladium or iridium. In catalysts which comprise cobalt and/or nickel as active metals, the amount of active metal can be up to 100% by weight and is usually in the range form 1 to 100% by weight, in particular 10 to 90% by weight, based on the total weight of the catalyst.

The supported catalysts can be used in the form of a powder. As a rule, such a powder has particle sizes in the range from 1 to 200 µm, in particular 1 to 100 µm. Pulverulent catalysts are suitable particularly when the catalyst is suspended in the reaction mixture to be hydrogenated (suspension mode). When using the catalysts in catalyst fixed beds, moldings are usually used; these are obtainable e.g. by extrusion or tableting and can have e.g. the shape of spheres, tablets, cylinders, strands, rings or hollow cylinders, stars and the like. The dimensions of these moldings usually fluctuate in the range from 0.5 mm to 25 mm. Catalyst strands with strand diameters of from 1.0 to 5 mm and strand lengths of from 2 to 25 mm are often used. Higher activities can generally be achieved with smaller strands, but these often do not exhibit adequate mechanical stability in the hydrogenation process. Consequently, very particular preference is given to using strands with strand diameters in the range from 1.5 to 3 mm. Preference is likewise given to spherical support materials with sphere diameters in the range from 1 to 10 mm, in particular 2 to 6 mm.

Preferred catalysts are those which comprise at least one active metal selected from ruthenium, rhodium and nickel, optionally in combination with one or more further active metals which are selected from the groups IB, VIIB and VIIIB of the Periodic Table (CAS version).

Particularly preferred catalysts are ruthenium-containing catalysts. These comprise ruthenium as active metal, optionally in combination with one or more further active metals. Preferred further active metals are selected from the groups IB, VIIB and VIIIB of the Periodic Table (CAS version). The catalysts may be unsupported catalysts or, preferably, supported catalysts. Examples of further active metals from the group VIIIB are e.g. platinum, rhodium, palladium, iridium, cobalt and nickel, which can also be used as a mixture of two or more thereof. Among the metals of subgroups IB and/or VIIB that can likewise be used, copper and/or rhenium, for example, are suitable. Preference is given to using ruthenium, on its own as active metal or together with platinum or iridium as active metal; very particular preference is given to using ruthenium on its own as active metal.

Preference is given in particular to ruthenium-containing catalysts in which the ruthenium, and also the optionally present further active metals, are arranged on a support material (ruthenium-containing supported catalysts). Suitable support materials for the ruthenium-containing supported catalysts are in principle the aforementioned support materials. Preference is given to silicon dioxide-containing support materials, in particular those which have a content of silicon dioxide of at least 90% by weight, based on the total weight of the support material. Preference is likewise given to aluminum oxide-containing support materials, in particular those which have a content of aluminum oxide (calculated as $Al_2O_3$) of at least 90% by weight, based on the total weight of the support material. Preferably, the support materials have a specific BET surface area, determined by $N_2$ adsorption in accordance with DIN 66131, of at least 30 $m^2/g$, in particular 50 to 1000 $m^2/g$. The amount of active metal is usually 0.05 to 10% by weight, preferably 0.1 to 3% by weight and in particular 0.1 to 1% by weight, based on the total weight of the ruthenium-containing supported catalyst.

Suitable ruthenium-containing catalysts are, for example, the catalysts specified in U.S. Pat. No. 3,027,398, DE 4407091, EP 258789, EP 813906, EP 1420012, WO 99/32427, WO 00/78704, WO 02/100536, WO 03/103830, WO 2005/61105, WO 2005/61106, WO 2006/136541 and WO2011082991. As regards the catalysts disclosed therein, reference is made to these documents.

Likewise preferred catalysts are rhodium-containing catalysts. These comprise rhodium as active metal, optionally in combination with one or more further active metals. Preferred further active metals are selected from the groups IB, VIIB or VIIIB of the Periodic Table (CAS version). The catalysts may be unsupported catalysts or preferably supported catalysts. Examples of further active metals from the group VIIIB are e.g. platinum, palladium, iridium, cobalt and nickel, which can also be used as a mixture of two or more thereof. Among the metals of subgroups IB and/or VIIB that can likewise be used, copper and/or rhenium, for example, are suitable. In these catalysts, rhodium is used on its own as active metal or together with platinum or iridium as active metal; very particular preference is given to using rhodium on its own as active metal. Suitable rhodium-containing catalysts are known for example from the publications specified above for rhenium-containing catalysts, can be prepared by the procedures indicated therein or are commercially available, e.g. the catalyst Escat 34 from Engelhard. For rhodium-containing supported catalysts, the aforementioned support materials are in principle suitable. Preference is given to silicon dioxide-containing support materials, in particular those which have a content of silicon dioxide of at least 90% by weight, based on the total weight of the support material. Preference is likewise given to aluminum oxide-containing support materials, in particular those which have a content of aluminum oxide (calculated as $Al_2O_3$) of at least 90% by weight, based on the total weight of the support material. The amount of active metal is usually 0.05 to 10% by weight, based on the total weight of the rhodium-containing supported catalyst.

Likewise preferred catalysts are nickel-containing catalysts. These comprise nickel as active metal, optionally in combination with one or more further active metals. Preferred further active metals are selected from the groups IB, VIIB or VIIIB of the Periodic Table (CAS version). The catalysts may be unsupported catalysts or preferably supported catalysts. Examples of further active metals from the group VIIIB are e.g. platinum, palladium, iridium and cobalt, which can also be used as a mixture of two or more thereof. Among the metals of subgroups IB and/or VIIB that can likewise be used, copper and/or rhenium, for example, are suitable. In these catalysts, nickel is preferably used on its own as active metal. Suitable nickel-containing catalysts are commercially available, for example the catalyst Ni5249P from BASF SE. For nickel-containing supported catalysts, the aforementioned support materials are in principle suitable. Preference is given to silicon dioxide-, aluminum oxide- and magnesium oxide-containing support materials, in particular those which consist to at least 90% by weight of such materials. The amount of active metal is usually 1 to 90% by weight, preferably 10 to 80% by weight and in particular 30 to 70% by weight, based on the total weight of the nickel-containing supported catalyst. Preference is also given to those nickel-containing catalysts which consist essentially exclusively of active metal, i.e. their amount of active metal is more than 90% by weight, e.g. 90 to 100% by weight.

According to one particularly preferred embodiment, a coated catalyst is used, in particular a coated catalyst which has, as active metal, ruthenium on its own or together with at least one further active metal of subgroups IB, VIIB or VIIIB of the Periodic Tables in the aforementioned amounts. Coated catalysts of this type are known in particular from WO 2006/136541 and also in the previously unpublished EP 09179201.0.

A coated catalyst of this type is a supported catalyst in which the majority of the active metal present in the catalyst is located in the vicinity of the surface of the catalyst. In particular, at least 60% by weight, particularly preferably at least 80% by weight, in each case based on the total amount of the active metal, are present to a penetration depth of at most 200 µm, i.e. in a shell with a distance of at most 200 µm from the surface of the catalyst particles. By contrast, only a very small amount, if any, of the active metal is present in the interior (core) of the catalyst. In the process according to the invention, very particular preference is given to using a shell catalyst in which no active metal can be detected in the interior of the catalyst, i.e. active metal is present only in the outermost shell, for example in a zone down to a penetration depth of 100 to 200 µm. The aforementioned data can be ascertained by means of SEM (scanning electron microscopy), EPMA (electron probe microanalysis)–EDXS (energy dispersive X-ray spectroscopy) and are averaged values. Further data as regards the aforementioned measurement methods and techniques can be found for example in "Spectroscopy in Catalysis" by J. W. Niemantsverdriet, VCH, 1995. As regards further details concerning the penetration depth of active metal, reference is made to WO 2006/136541, in particular to p. 7, lines 6 to 12.

Preferred coated catalysts have a content of active metal in the range from 0.05 to 1% by weight, in particular 0.1 to 0.5% by weight, particularly preferably 0.25 to 0.35% by weight, in each case based on the total weight of the catalyst.

For the hydrogenation according to the invention in step b), coated catalysts with a support material based on silicon dioxide, in general amorphous silicon dioxide, are particularly preferred. In this connection, the term "amorphous" is understood as meaning that the fraction of crystalline silicon dioxide phases constitutes less than 10% by weight of the support material. The support materials used for producing the catalysts can however have superstructures which are formed by regular arrangement of pores in the carrier material. Suitable support materials are in principle amorphous silicon dioxide grades which consist at least to 90% by weight of silicon dioxide, in which case the remaining 10% by weight, preferably not more than 5% by weight, of the support material can also be a different oxidic material, e.g. MgO, CaO, $TiO_2$, $ZrO_2$, $Fe_2O_3$ and/or alkali metal oxide. In a preferred embodiment of the coated catalyst, the support material is halogen-free, in particular chlorine-free, i.e. the content of halogen in the support material is less than 500 ppm by weight, e.g. in the range from 0 to 400 ppm by weight. Consequently, preference is given to a coated catalyst which comprises less than 0.05% by weight of halide (determined by ion chromatography), based on the total weight of the catalyst. Preference is given to support materials which have a specific surface area in the range from 30 to 700 $m^2/g$, preferably 30 to 450 $m^2/g$, (BET surface area in accordance with DIN 66131). Suitable amorphous support materials based on silicon dioxide are known to the person skilled in the art and are commercially available (see e.g. O. W. Flörke, "Silica" in Ullmann's Encyclopedia of Industrial Chemistry, 6th Edition on CD-ROM). They can have been produced either from natural origin or else synthetically. Examples of suitable amorphous support materials based on silicon dioxide are silica gels, kieselguhr, pyrogenic silicas and precipitated silicas. In a preferred embodiment of the invention, the catalysts used have silica gels as support materials. Depending on the configuration of the coated catalyst, the support material can take various forms. If the process according to the invention in which the coated catalysts are used is designed as a suspension process, then the support material will usually be used in the form of a finely divided powder for producing the catalysts used. Preferably, the powder has particle sizes in the range from 1 to 200 μm in particular 1 to 100 μm. When using the coated catalyst according to the invention in catalyst fixed beds, moldings, as described above, of the support material are usually used.

In a particularly preferred embodiment, the support material of the coated catalyst used, which is in particular a support material based on silicon dioxide, has a pore volume in the range from 0.6 to 1.0 ml/g, preferably in the range from 0.65 to 0.9 ml/g, for example from 0.7 to 0.8 ml/g, determined by Hg porosimetry (DIN 66133), and a BET surface area in the range from 280 to 500 $m^2/g$, preferably in the range from 280 to 400 $m^2/g$, very particularly preferably in the range from 300 to 350 $m^2/g$. Preferably, in coated catalysts of this type, at least 90% of the pores present have a diameter of from 6 to 12 nm, preferably 7 toll nm, particularly preferably 8 to 10 nm. The pore diameter can be determined by means of methods known to the person skilled in the art, for example by Hg porosimetry or $N_2$-physisorption. In a preferred embodiment, at least 95%, particularly preferably at least 98%, of the pores present have a pore diameter of from 6 to 12 nm, preferably 7 to 11 nm, particularly preferably 8 to 10 nm.

In a preferred embodiment, no pores which are smaller than 5 nm are present in these coated catalysts. Furthermore, no pores larger than 25 nm, in particular larger than 15 nm, are preferably present in these coated catalysts. In this connection "no pores" means that no pores with these diameters are found using customary measurement methods, for example Hg porosimetry or $N_2$ physisorption.

In preferred coated catalysts, the dispersity of the active metal is preferably 30 to 60% and particularly preferably 30 to 50%. Methods for measuring the dispersity of the active metal are known to the person skilled in the art and include, for example, pulse chemisorption, in which the determination of the precious metal dispersion (specific metal surface area, crystallite size) is carried out with a CO pulse method (DIN 66136(1-3)).

The hydrogenation process according to the invention can be carried out in the liquid phase or in the gas phase. Preference is given to carrying out the hydrogenation process according to the invention in the liquid phase.

The hydrogenation process according to the invention can be carried out either in the presence or the absence of a solvent or diluent, i.e. it is not absolutely necessary to carry out the hydrogenation in solution. Solvents or diluents which can be used are any suitable solvents or diluents. Suitable solvents or diluents are in principle those which are able to dissolve the organic compound to be hydrogenated as completely as possible or are completely miscible therewith and which are inert, i.e. are not hydrogenated, under the hydrogenation conditions. Examples of suitable solvents are cyclic and acyclic ethers having preferably 4 to 8 carbon atoms, e.g. tetrahydrofuran, dioxane, methyl tert-butyl ether, dimethoxyethane, dimethoxypropane, dimethyldiethylene glycol, aliphatic alcohols having preferably 1 to 6 carbon atoms such as methanol, ethanol, n- or isopropanol, n-, 2-, iso- or tert-butanol, carboxylic acid esters of aliphatic carboxylic acids having preferably 3 to 8 carbon atoms such as methyl acetate, ethyl acetate, propyl acetate or butyl acetate, methyl propionate, ethyl propionate, butyl propionate, and also aliphatic ether alcohols such as methoxy propanol and cycloaliphatic compounds such as cyclohexane, methylcyclohexane and dimethylcyclohexane. The amount of solvent or diluent used is not limited in a particular manner and can be freely chosen as necessary, although when using a solvent preference is given to those amounts which lead to a 3 to 70% strength by weight solution of the organic compound provided for the hydrogenation.

In one embodiment of the invention, the step b) according to the invention is carried out without dilution.

The actual hydrogenation usually takes place analogously to the known hydrogenation processes for the hydrogenation of organic compounds which have hydrogenable groups, preferably for the hydrogenation of a carbocyclic aromatic group to give the corresponding carbocyclic aliphatic groups, as described in the prior art cited at the start. For this, the organic compound is brought into contact, as the liquid phase or gas phase, preferably as liquid phase, with the catalyst in the presence of hydrogen. The liquid phase can be passed over a fluidized catalyst bed (fluidized bed mode) or a fixed catalyst bed (fixed bed mode).

The hydrogenation can be designed to be continuous or discontinuous, with the continuous procedure being preferred. Preferably, the process according to the invention is carried out in trickle reactors or in flooded mode by the fixed bed mode, the procedure in trickle reactors being particularly preferred. In particular, the compound to be hydrogenated is used without dilution, i.e. extensive absence of organic diluents (solvent content preferably <10%). The hydrogen here can be passed over the catalyst either cocurrently with the solution of the starting material to be hydrogenated, or else countercurrently. The hydrogenation can also be carried out discontinuously by the batch mode. In this case, the hydrogenation will preferably be carried out in an organic solvent or diluent.

In the case of a discontinuous procedure of the process according to the invention, in step b), the catalyst is typically used in an amount such that the concentration of ruthenium in the reaction mixture used for the hydrogenation is in the range from 10 to 10 000 ppm, in particular in the range from 50 to 5000 ppm, specifically in the range form 100 to 1000 ppm.

The hydrogenation typically takes place at a hydrogen pressure in the range from 5 to 50 MPa, in particular in the range from 10 to 30 MPa. The hydrogen can be fed into the reactor as it is, or diluted with an inert material, for example nitrogen or argon.

The hydrogenation in step b) typically takes place at temperatures above 50° C., in particular in the range from 100 to 250° C.

Apparatuses suitable for carrying out the hydrogenation are known to the person skilled in the art and are determined primarily by the mode of operation. Suitable apparatuses for carrying out a hydrogenation according to the hydrogenation on the fluidized catalyst bed and on the fixed catalyst bed are known e.g. from Ullmann's Encyclopedia of Industrial Chemisty, $4^{th}$ edition, volume 13, p. 135 ff., and also from P. N. Rylander, "Hydrogenation and Dehydrogenation" in Ullmann's Encyclopedia of Industrial Chemistry, $5^{th}$ edition on CD-ROM.

Compounds of the formula (Ia), where $R^1$ and $R^2$, independently of one another, are selected from groups of the formula $(C_{3-7}$-cycloalkyl$)_x$-$(C_{1-7}$-alkyl$)_y$, wherein either each of x and y is 1, or one of the variables x and y is 1 and the other is 0, and $R^1$ and $R^2$ together comprise in total 4 to 11 carbon atoms, 5 to 11 carbon atoms, in particular 4 to 8 carbon atoms and preferably 4 or 5 carbon atoms, are likewise provided by the invention. If $R^1$ and $R^2$ together comprise in total 4 carbon atoms, each of $R^1$ and $R^2$ is preferably ethyl. Compounds of the formula (Ia) according to the invention can thus be selected for example from 1-cyclohexyl-3-methyl-3-heptanol, 1-cyclohexyl-3-methyl-3-octanol, 1-cyclohexyl-3-methyl-3-nonanol, 1-cyclohexyl-3,4-dimethyl-3-octanol, 1-cyclohexyl-3,5-dimethyl-3-octanol, 1-cyclohexyl-3,6-dimethyl-3-octanol, 1-cyclohexyl-3,7-dimethyl-3-octanol, 1-cyclohexyl-3,4,4-trimethyl-3-heptanol, 1-cyclohexyl-3,5,5-trimethyl-3-heptanol, 1-cyclohexyl-3,6,6-trimethyl-3-heptanol, 1-cyclohexyl-5-ethyl-3-methyl-3-heptanol, 1-cyclohexyl-3,5-dimethyl-3-heptanol, 2,4-dicyclohexyl-2-methyl-2-butanol, 1-cyclohexyl-4-cyclopentyl-3-methyl-3-pentanol, 1-cyclohexyl-3-ethyl-3-hexanol, 1-cyclohexyl-3-ethyl-3-heptanol, 1-cyclohexyl-3-ethyl-3-octanol and 1-cyclohexyl-3-ethyl-3-nonanol.

The present invention also provides compositions comprising a compound of the formula (Ia)

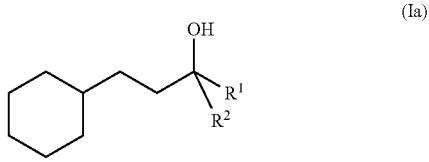
(Ia)

and a compound of the formula (Ib)

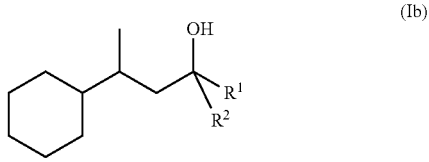
(Ib)

where $R^1$ and $R^2$, independently of one another, are selected from groups of the formula $(C_{3-7}\text{-cycloalkyl})_x\text{-}(C_{1-7}\text{-alkyl})_y$, as defined above, and $R^1$ and $R^2$ together comprise in total 3 to 11 carbon atoms, in particular 3 to 8 carbon atoms, preferably 3 to 5 carbon atoms and particularly preferably 3 carbon atoms.

In these compositions, the weight ratio of the compound(s) of the formula (Ia) to the compound(s) of the formula (Ib) is in general in the range from 50:1 to 1000:1. Compositions of this kind can also comprise small amounts of a corresponding compound of the formula (IV)

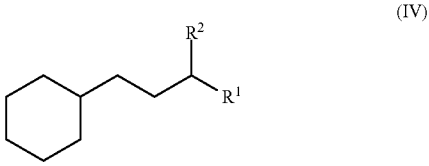
(IV)

and optionally of a corresponding compound of the formula (V)

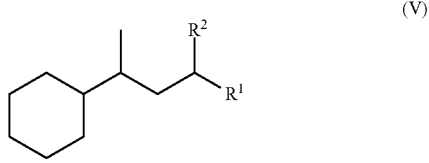
(V)

which are formed by superreduction of the corresponding compounds of the formula (IIIa) or compounds of the formula (IIIb). The weight fraction of the total amount of the compound of the formula (IV) and optionally of the compound of the formula (V) will generally not exceed 10% by weight, in particular 5% by weight, based on the corresponding compound of the formula (Ia) and is, if present, in the range from 0.01 to 10% by weight, in particular in the range from 0.01 to 5% by weight, based on the corresponding compound of the formula (Ia). It is of course also possible to separate off compounds of the formula (IV) and optionally present compounds of the formula (V), e.g. by a distillative route, such that the total amount of compound of the formula (IV) and optionally present compound of the formula (V) is less than 1% by weight, in particular less than 0.5% by weight or less than 0.1% by weight, based on the corresponding compound of the formula (Ia). A specific composition is concentrates, i.e. compositions which consist essentially, i.e. to at least 95% by weight, in particular at least 98% by weight and specifically at least 99% by weight or at least 99.5% by weight, of a compound of the formula (Ia) and small amounts of corresponding compound of the formula (Ib), e.g. compositions in which the weight ratio of the compound of the formula (Ia) to the corresponding compound of the formula (Ib) is in the range from 50:1 to 1000:1.

These concentrates can comprise corresponding compounds of the formula (IV) and optionally corresponding compounds of the formula (V) in the amounts specified above. Compositions in which the weight ratio of the compound of the formula (Ia) to the corresponding compound of the formula (Ib) is outside of the ranges specified here, can be prepared by mixing the compound of the formula (Ia) with the desired amount of compound of the formula (Ib). Compositions of this type are naturally likewise provided by the present invention.

A compound of the formula (Ib) can be prepared from a corresponding compound of the formula (IIIb) analogously to step b), i.e. by a process comprising a heterogeneous-catalytic hydrogenation of the compound of the formula (IIIb). As regards the hydrogenation of the compound of the formula (IIIb), reference is made to the statements above relating to the hydrogenation in step b) in their entirety.

Here, the procedure may involve firstly preparing a compound of the formula (IIIb) in a targeted manner and then subjecting it to a heterogeneous-catalytic hydrogenation analogously to step b) described previously. A compound of the formula (IIIb) can be prepared in a targeted manner by reacting α-methylstyrene with a corresponding compound of the formula (II) under the conditions specified above for step a).

However, the procedure may also involve firstly preparing a composition from a compound of the formula (IIIa) and a corresponding compound of the formula (IIIb), e.g. in the manner described above for step a), subjecting this composition to a heterogeneous-catalytic hydrogenation analogously to step b) described previously, and separating the resulting composition, which comprises a corresponding compound of the formula (Ia) and a corresponding compound of the formula (Ib), into its constituents by distillation. The distillation can be carried out analogously to customary fractional distillation processes. Suitable devices for this are known to the person skilled in the art. The necessary conditions can be ascertained by routine experiments. As a rule, the distillation takes place at reduced pressure.

In the compounds of the formulae (Ia) and (Ib) according to the invention in which $R^1$ and $R^2$ are different, the chiral carbon atom carrying the hydroxyl group can have a different configuration. Accordingly, the present invention also relates to the individual enantiomers and enantiomer mixtures, e.g. a racemate, of the compounds of the formula (Ia) or of the formula (Ib) according to the invention. The enantiomers can be separated from one another with the help of generally known processes, e.g. by means of crystallization, by means of chiral column chromatography or by means of conversion to diastereomers, which are separated from one another by conventional chromatography and distillation processes and are then converted again into the now enantiomerically pure starting compounds. Moreover, the compounds of the formula (Ib) according to the invention can have a different configuration at the chiral carbon atom carrying the cyclohexyl group. Accordingly, the present invention also relates to individual diastereomers and diastereomer mixtures of the compounds of the formula (Ib) according to the invention. The diastereomers can be separated from one another on account of their different physical properties by conventional processes, such as e.g. chromatography and distillation processes.

Compounds of the formulae (Ia) and (Ib) and the compositions and concentrates likewise described here are odorous substances which can be used as fragrances or aroma substances and in particular in cosmetic compositions, textile detergents and cleaners for hard surfaces.

The invention thus also relates to cosmetic compositions, textile detergents and cleaners for hard surfaces comprising:
i. one or more compound(s) of the formula (Ia), in particular those in which $R^1$ and $R^2$ together comprise in total 3 to 8 carbon atoms and preferably 3 to 5 carbon atoms, particularly preferably 1-cyclohexyl-3-methyl-3-pentanol, or
ii. a composition comprising a compound of the formula (Ia) and a corresponding compound of the formula (Ib), in particular those in which $R^1$ and $R^2$ comprise together in total 3 to 8 carbon atoms and preferably 3 to 5 carbon atoms, particularly preferably where $R^1$ is methyl and $R^2$ is ethyl.

Preferably, the compound(s) i. and composition ii., respectively, are comprised as additives, i.e. said cosmetic compositions, textile detergents and cleaners for hard surfaces, respectively, comprise, in addition to i. or ii., compounds or compositions, which are suitable as use as cosmetic compositions, textile detergents and cleaners for hard surfaces.

Examples of suitable cosmetic compositions are in principle all cosmetic compositions which usually comprise fragrances. These include, for example, Eaux-de-Parfum, Eaux-de-Toilette, Eaux-de-Cologne, after shave products such as lotions and creams, preshave products, perfumed freshening wipes, hair removal creams and lotions, tanning creams and lotions, haircare compositions such as shampoos, hair rinses, hair setting compositions, hair gels, hair tinting compositions, hair waxes, hairsprays, setting foams, hair mousses, end fluids, neutralizers for permanent waves, hair colorants and bleaches or "hot-oil treatments", also skin cleansers such as soaps, washing gels, shower gels, bodycare compositions such as creams, oils, lotions and the like for the skin, such as e.g. products for caring for the hands, the face or the feet, sunscreens, deodorants and antiperspirants, skin disinfectants, insect repellents, and also decorative cosmetic products. Depending on the field of use, the cosmetic compositions can be formulated as aqueous or alcoholic liquid, oil, (aerosol) spray, (aerosol) foam, mousse, gel, gel spray, cream, lotion, powder, tabs or wax.

Detergents and cleaners include compositions for the cleaning and/or disinfection of surfaces, such as, for example, household cleaners, neutral cleaners, toilet cleaners, floor cleaners, carpet cleaners, window cleaners, polishes, furniture care products, liquid and solid dishwashing detergents, liquid and solid machine dishwashing detergents, also compositions for the cleaning or treatment of textiles such as solid, semisolid or liquid textile detergents, laundry aftertreatment compositions, fabric softeners, ironing aids, textile fresheners, fabric preconditioners, washing soaps, washing tablets and the like.

Furthermore, the compounds and compositions according to the invention can be used as fragrance constituent in other fragrance-containing products such as air purifiers, lamp oils, candles, room air improvers, toilet blocks and the like.

The compound of the formula (Ia) in the compositions according to the invention, cosmetic compositions, textile detergents, cleaners and uses can for example be selected from 1-cyclohexyl-3-methyl-3-pentanol, 1-cyclohexyl-3-methyl-3-hexanol, 1-cyclohexyl-3-methyl-3-heptanol, 1-cyclohexyl-3-methyl-3-octanol, 1-cyclohexyl-3-methyl-3-nonanol, 1-cyclohexyl-3,4-dimethyl-3-octanol, 1-cyclohexyl-3,5-dimethyl-3-octanol, 1-cyclohexyl-3,6-dimethyl-3-octanol, 1-cyclohexyl-3,7-dimethyl-3-octanol, 1-cyclohexyl-3,4,4-trimethyl-3-heptanol, 1-cyclohexyl-3,5,5-trimethyl-3-heptanol, 1-cyclohexyl-3,6,6-trinnethyl-3-heptanol, 1-cyclohexyl-5-ethyl-3-methyl-3-heptanol, 1-cyclohexyl-3,5-dimethyl-3-heptanol, 2,4-Dicyclohexyl-2-methyl-2-butanol, 1-cyclohexyl-4-cyclopentyl-3-methyl-3-pentanol, 1-cyclohexyl-3-ethyl-3-hexanol, 1-cyclohexyl-3-ethyl-3-heptanol, 1-cyclohexyl-3-ethyl-3-octanol and 1-cyclohexyl-3-ethyl-3-nonanol.

The invention is illustrated in more detail by reference to the following examples:

EXAMPLE 1

Preparation of the Hydrogenated Catalyst

The support material used was a spherical SiO2 support (type AF125 from BASF SE) with a sphere diameter of 3 to 5 mm and a bulk density of 0.49 kg/l. The BET surface area was 337 m2/g, the water absorption (WA) was 0.83 ml/g. For the impregnation, a 14.25% by weight ruthenium(III) acetate solution in acetic acid (from Umicore) was used.

200 g of support were introduced as initial charge into a round-bottomed flask. 15 g of the ruthenium acetate solution were diluted to 150 ml with distilled water (90% WA). The support material was introduced as initial charge into the distillation column of a rotary evaporator and the first quarter of the solution was pumped onto the support material with a slight vacuum at 3 to 6 rpm. When the addition was complete, the support was left in the rotary evaporator for a further 10 minutes at 3 to 6 rpm in order to homogenize the catalyst. This impregnation/homogenization step was repeated three times until all of the solution had been applied to the support. The support material treated in this way was dried under agitation in the rotary dryer at 140° C., then reduced for 3 h at 200° C. in a stream of hydrogen (20 l/h $H_2$; 101/h $N_2$) and passivated at 25° C. (5% air in $N_2$, 2 h). The resulting catalyst A according to the invention comprised 0.34% by weight of ruthenium, based on the total weight of the catalyst.

Step a) EXAMPLE 2

Preparation of 3-methyl-1-phenyl-3-pentanol

The reaction of styrene and 2-butanol was carried out in a continuously operated laboratory plant. This comprised a 300 ml autoclave which was operated with pressure regulation. Thus, the amount removed corresponded at all times to the amount introduced. The removed reaction mixture was cooled, decompressed and collected in a discharge container.

A solution of styrene in 2-butanol (20% by weight, 100 g/h) was pumped continuously at an average temperature of 390° C. in the reactor through the laboratory plant. The conversion of styrene was 84.0% and, in the steady state, 14.7 g/h of 3-methyl-1-phenyl-3-pentanol were obtained.

Step b)- EXAMPLE 3

Preparation of 1-cyclohexyl-3-methyl-3-pentanol

A 300 ml autoclave was initially charged with 5.6 g of 3-methyl-1-phenyl-3-pentanol, dissolved in 94.4 g of tetrahydrofuran, and 1.6 g of a catalyst prepared according to Example 1 (0.35% ruthenium on silicon dioxide). The autoclave was flushed three times with nitrogen and then hydrogenated for 10 hours at 160° C. and a hydrogen pressure of 160 bar. The product was analyzed by gas chromatography (polydimethylsiloxane DB1, 30 m, internal diameter: 0.25 mm, film thickness: 0.25 μm, 50° C., 5 min isotherm, −6° C./min, 290° C., 219 min isotherm). The conversion was 99.9%, the selectivity 93%.

The invention claimed is:

1. A process for the preparation of a composition comprising a compound of formula (Ia) and a compound of formula (Ib)

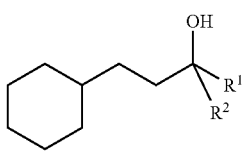

(Ia)

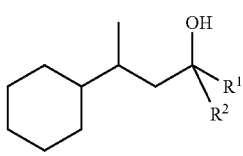

(Ib)

the process comprising:
a) reacting styrene with a compound of the formula (II)

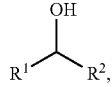

(II)

to provide a compound of formula (IIIa) and a compound of formula (IIIb)

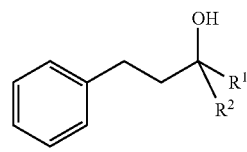

(IIIa)

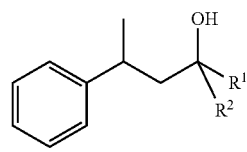

(IIIb)

and
b) the heterogeneous-catalytic hydrogenation of the compounds of the formula (IIIa) and formula (IIIb) to give the compounds of the formula (Ia) and the formula (Ib), where $R^1$ and $R^2$, independently of one another, are selected from $C_{3-7}$-cycloalkyl-$C_{1-7}$-alkyl-, $C_{3-7}$-cycloalkyl-, or $C_{1-7}$-alkyl-, and $R^1$ and $R^2$ together comprise in total 3 to 11 carbon atoms.

2. The process according to claim 1, wherein $R^1$ and $R^2$, independently of one another, are selected from $C_{1-7}$-alkyl-, $C_{3-7}$-cycloalkyl or $C_{4-7}$-cycloalkylalkyl.

3. The process according to claim 1, wherein the reaction in step a) takes place under conditions under which the compound of the formula (II) is present in a supercritical state.

4. The process according to claim 1, wherein the reaction in step a) takes place at a temperature in the range from 250 to 500° C. and a pressure in the range from 5 to 50 MPa.

5. The process according to claim 1, wherein the molar ratio of the styrene used in step a) to the compound of the formula (II) used in step a) is in the range from 1:5 to 1:200.

6. The process according to claim 1, wherein the catalyst used in step b) comprises at least one active metal selected from the group consisting of palladium, platinum, cobalt, nickel, rhodium, iridium and ruthenium.

7. The process according to claim 6, wherein the catalyst used in step b) comprises ruthenium as active metal.

8. The process according to claim 6, wherein the catalyst used in step b) comprises at least one further active metal of sub-groups IB, VIIB or VIIIB of the Periodic Table (CAS version).

9. The process according to claim 1, wherein step b) is carried out in trickle mode.

10. The process according to claim 1, wherein $R^1$ is methyl and $R^2$ is ethyl.

11. A composition comprising a compound of the formula (Ia)

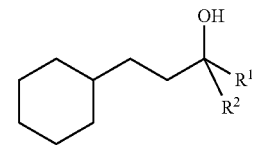

(Ia)

and a compound of the formula (Ib)

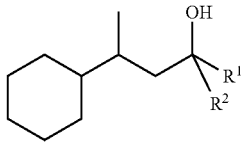

where $R^1$ and $R^2$, independently of one another, are selected from $C_{3-7}$-cycloalkyl-$C_{1-7}$-alkyl-, $C_{3-7}$-cycloalkyl-, and $C_{1-7}$-alkyl-, and $R^1$ and $R^2$ together comprise in total 3 to 11 carbon atoms.

12. The composition according to claim 11, wherein $R^1$ and $R^2$, independently of one another, are selected from the group consisting of $C_{1-7}$-alkyl-, $C_{3-7}$-cycloalkyl and $C_{4-7}$-cycloalkylalkyl.

13. The composition according to claim 11, where $R^1$ is methyl and $R^2$ is ethyl.

14. A cosmetic composition comprising a compound of the formula (Ia) and a compound of formula (Ib)

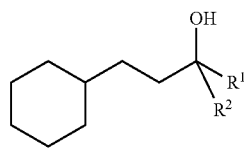

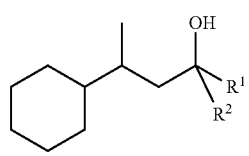

where $R^1$ and $R^2$, independently of one another, are selected from $C_{3-7}$-cycloalkyl-$C_{1-7}$-alkyl-, $C_{3-7}$-cycloalkyl-, and $C_{1-7}$-alkyl-, and $R^1$ and $R^2$ together comprise in total 3 to 11 carbon atoms, wherein the cosmetic composition is formulated as aqueous or alcoholic liquid, oil, spray, foam, mousse, gel, gel spray, cream, lotion, tabs or wax.

15. The cosmetic composition, textile detergent or cleaner for hard surfaces according to claim 14, wherein $R^1$ is methyl and $R^2$ is ethyl.

* * * * *